United States Patent
Christiansen

(10) Patent No.: US 8,876,854 B2
(45) Date of Patent: Nov. 4, 2014

(54) IMPLANT RELEASE MECHANISM

(75) Inventor: Frank K. Christiansen, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 206 days.

(21) Appl. No.: 12/936,107

(22) PCT Filed: Apr. 3, 2009

(86) PCT No.: PCT/US2009/039448
§ 371 (c)(1),
(2), (4) Date: Nov. 8, 2010

(87) PCT Pub. No.: WO2009/146128
PCT Pub. Date: Dec. 3, 2009

(65) Prior Publication Data
US 2011/0046611 A1 Feb. 24, 2011

Related U.S. Application Data

(60) Provisional application No. 61/072,903, filed on Apr. 3, 2008.

(51) Int. Cl.
*A61M 29/00* (2006.01)
*A61F 2/06* (2013.01)
*A61F 2/95* (2013.01)

(52) U.S. Cl.
CPC ........... *A61F 2/95* (2013.01); *A61F 2002/9534* (2013.01)
USPC ............ 606/200; 606/193; 606/194; 606/198

(58) Field of Classification Search
CPC .................. A61B 17/12099; A61B 17/12104; A61B 17/12109; A61B 17/12113; A61B 17/12118; A61B 17/12122; A61B 17/1214; A61B 17/12145; A61B 17/1215; A61B 14/12154; A61B 17/12159; A61B 17/12163
USPC ......... 606/191, 195, 198, 200, 194; 623/1.11, 623/1.12, 1.23, 1.34
See application file for complete search history.

(56) References Cited

U.S. PATENT DOCUMENTS

| | | | | |
|---|---|---|---|---|
| 5,261,916 A | * | 11/1993 | Engelson | 606/108 |
| 5,925,059 A | * | 7/1999 | Palermo et al. | 606/191 |
| 6,346,118 B1 | | 2/2002 | Baker et al. | |

(Continued)

FOREIGN PATENT DOCUMENTS

| WO | WO 98/53761 | 12/1998 |
|---|---|---|
| WO | WO 99/49809 | 10/1999 |

(Continued)

*Primary Examiner* — Tuan V Nguyen
(74) *Attorney, Agent, or Firm* — Brinks Gilson & Lione

(57) ABSTRACT

A delivery assembly (10) for an implant (30) includes a release mechanism with a locking element (52) and a blocking member (56). The locking element (52) includes a latching pin (14) that engages with an eyelet (54) in the implant (30) to attach the implant (30) to a distal end of an inner catheter (36). The blocking member (56) prevents premature disengagement of the latching pin (14) from the implant (30). Withdrawal of the blocking member (56) allows disengagement of the latching pin (14). The locking pin (52) and the blocking member (56) extend along the lumen of the inner catheter (36) from a handle (12) such that a guide wire (34) is also able to extend through the lumen of the inner catheter (36). The locking pin (52) and the blocking member (56) preferably have a crescent-shaped transverse cross section. The release mechanism allows retrieval of the implant (30).

17 Claims, 5 Drawing Sheets

(56) References Cited

U.S. PATENT DOCUMENTS

| | | | |
|---|---|---|---|
| 7,371,252 B2 * | 5/2008 | Balgobin et al. | 606/200 |
| 7,708,755 B2 * | 5/2010 | Davis et al. | 606/200 |
| 2004/0220585 A1 * | 11/2004 | Nikolchev | 606/108 |
| 2005/0060018 A1 * | 3/2005 | Dittman | 623/1.11 |
| 2006/0276825 A1 * | 12/2006 | Mitelberg et al. | 606/200 |
| 2006/0276830 A1 * | 12/2006 | Balgobin et al. | 606/200 |
| 2006/0276833 A1 * | 12/2006 | Balgobin et al. | 606/200 |
| 2007/0270903 A1 * | 11/2007 | Davis, III et al. | 606/200 |
| 2007/0299422 A1 | 12/2007 | Inganas et al. | |

FOREIGN PATENT DOCUMENTS

| | | |
|---|---|---|
| WO | WO 2004/087006 | 10/2004 |
| WO | WO 2009/146128 | 12/2009 |

* cited by examiner

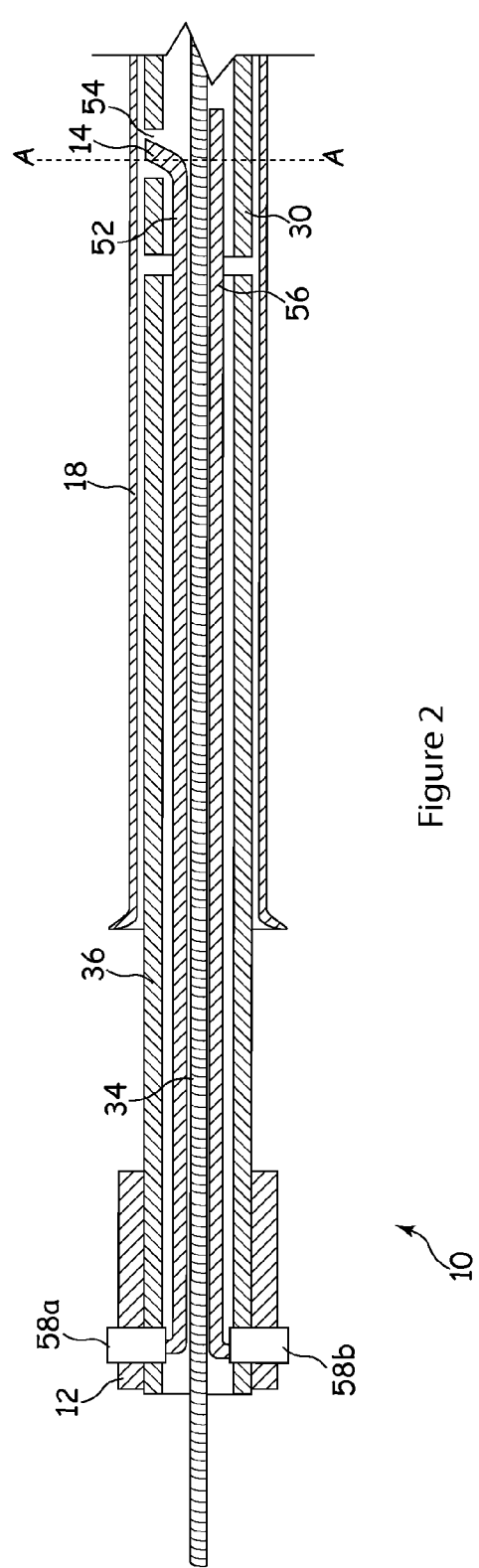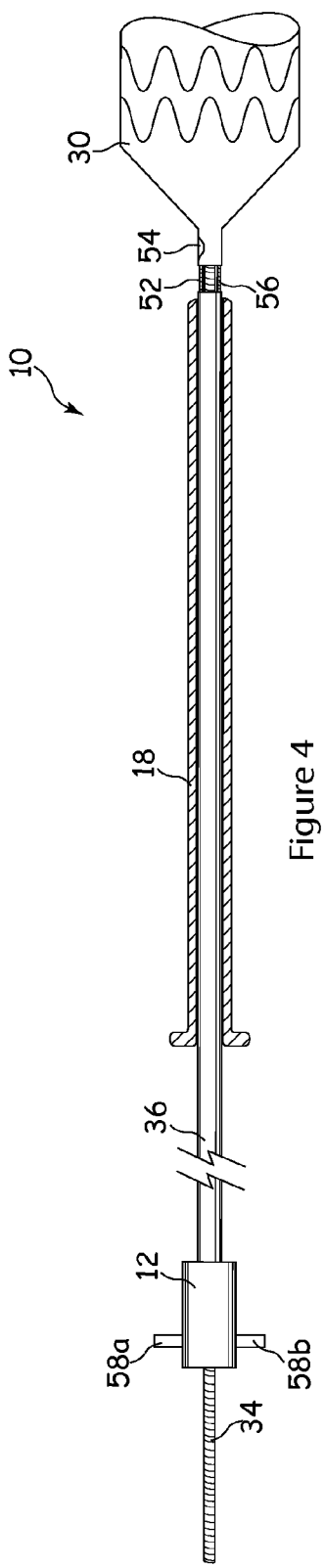

IMPLANT RELEASE MECHANISM

CROSS REFERENCE TO RELATED APPLICATIONS

This application claims the benefit of priority to PCT/US2009/039448 filed Apr. 3, 2009 which claims the benefit of Provisional Patent Application Ser. No. 61/072,903 filed Apr. 3, 2008, the entire contents of which are hereby incorporated herein by reference.

TECHNICAL FIELD

The present invention relates to a release mechanism for releasing an implant from a deployment device, for example for releasing a frame or a frame with a graft. In particular the release mechanism can be used in conjunction with over-the-wire delivery of an implant. The present invention relates also to a deployment device including the release mechanism, and to an implant that may be delivered by the deployment device.

BACKGROUND ART

Delivery devices employing catheters have been used for medical procedures, including procedures for establishing, re-establishing or maintaining passages, cavities or lumens in vessels, organs or ducts in human and veterinary patients, occlusion of such vessels, delivering medical treatments, and other interventions. For these procedures, it is known to deliver an implant by means of a catheter, often intraluminally.

Use of a guide wire over which an implant deployment device is passed in order to deliver an implant to a location within a patient's vasculature requiring treatment greatly facilitates the delivery process. However, accommodation of a guide wire presents special design problems for other components of an implant delivery system.

One problem with prior art release mechanisms is that they cannot be used in conjunction with a guide wire. Another problem is that known mechanisms for release and retrieval of an implant are complex and thus take up a lot of space within an introducer. This may particularly be a problem where immediate vascular occlusion is desired.

SUMMARY

When a prosthesis is implanted into a patient, the device to be implanted may be held onto the catheter in a compressed state and then released from the catheter so as to expand to its normal operating state, prior to withdrawal of the catheter from the patient to leave the implant in position.

Delivery mechanisms involve positioning the implant at a distal end of a delivery device, that is, at an end furthest from the external manipulation end used by the clinician during the deployment procedure. The prosthesis or implant may be held to the distal end of the catheter by a suitable restraining mechanism, restraining wires being one example. The implant may be covered with a sheath in order to protect the implant and also the patient's lumens or organs during the delivery process.

After correct positioning and release, the implant is then expanded. This can be done automatically, if the implant is of the self-expanding type. Otherwise suitable expanding mechanism can be used, such as an expansion balloon.

The present invention seeks to provide an improved implant release mechanism. According to a first aspect of the present invention, there is provided an implant release mechanism for use over a guide wire, including: a releasable coupling member for maintaining attachment of an implant to be deployed to a deployment device; and a blocking member for blocking release of the coupling member; wherein removal of the blocking member allows release of the coupling member, and thus detachment of an implant. The above arrangement provides a mechanism for controlled release of an implant. Furthermore, the mechanism can be used over a guide wire.

In a preferred embodiment, the releasable coupling member is operable to reattach a released implant to a delivery device. This enables a surgeon or clinician to adjust the position of an implant during deployment to ensure that it is correctly replaced. Furthermore, the mechanism can be used to remove an implant from a patient where the implant is intended to be only temporary. The releasable coupling member may be arranged to attach an implant distally of a catheter part of a deployment device.

Preferably, the coupling member, the blocking member and a guide wire together substantially fill a lumen of an implant at least at an implant-coupling portion. In this way, release of a coupling member from an implant is only possible once the blocking member has been moved.

In a preferred embodiment, the coupling member may extend longitudinally through a bore of a catheter of an implant deployment device from a handle at a proximal end of the device to an implant at the distal end of the device, and the distal end of the coupling member may engage with an implant. The coupling member may include a radially extending projection able to engage with an implant.

In an embodiment, the blocking member extends at least as far as the position of the coupling member projection and the blocking member prevents radially inward movement of the coupling member and thus disengagement of the projection from an implant.

The coupling member and the blocking member may extend longitudinally through a bore of a catheter of an implant deployment device, the coupling member and the blocking member may be arranged approximately 180° from one another, and the coupling member and the blocking member may together define a longitudinal channel for a guide wire. In this arrangement, the coupling member, the blocking member, and the guide wire substantially fill a bore of a catheter of an implant deployment device.

At least one of the coupling member and the blocking member may have a transverse cross section that is substantially crescent-shaped such that it extends partially around an inner wall of a catheter of an implant deployment device. This arrangement assists in ensuring that the coupling member, the guide wire and the blocking member substantially fill a bore of a catheter of an implant deployment device.

According to a second aspect of the present invention, there is provided an implant deployment device including a release mechanism as specified above.

According to a third aspect of the present invention there is provided an implant for delivery by the above-specified implant deployment device, the implant including an engagement portion for coupling to the releasable coupling member.

Preferably, the engagement portion includes an aperture. In a preferred embodiment, the engagement portion includes a substantially tubular member having an aperture in a wall thereof. The engagement portion may include a substantially non-expandable tubular member.

The implant may be an occlusion device, a frame, a frame with a graft, or a filter. Preferably, the implant is an occlusion device that provides substantially immediate vascular occlusion.

According to a fourth aspect of the present invention, there is provided an implant deployment device having an implant as specified above attached thereto by a coupling member.

Further aspects, features, and advantages of the invention will become apparent from consideration of the following description and the appended claims when taken in connection with the accompanying drawings.

BRIEF DESCRIPTION OF THE DRAWINGS

Embodiments of the present invention are described below, by way of example only, with reference to the accompanying drawings, in which:

FIG. 2 is an enlarged view of part of the device of FIG. 1;

FIG. 4 is a side view of the implant delivery device of FIGS. 1 to 3 after withdrawal of the introducer sheath;

DESCRIPTION OF THE PREFERRED EMBODIMENTS

It is to be understood that the Figures are schematic and do not show the various components to their actual scale. In many instances, the Figures show scaled up components to assist in the understanding of the features disclosed therein.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as a frame or an occlusion device, the term proximal refers to a location that in use is closest to the patient's heart, in the case of a vascular implant, and the term distal refers to a location furthest from the patient's heart.

Figure 1:
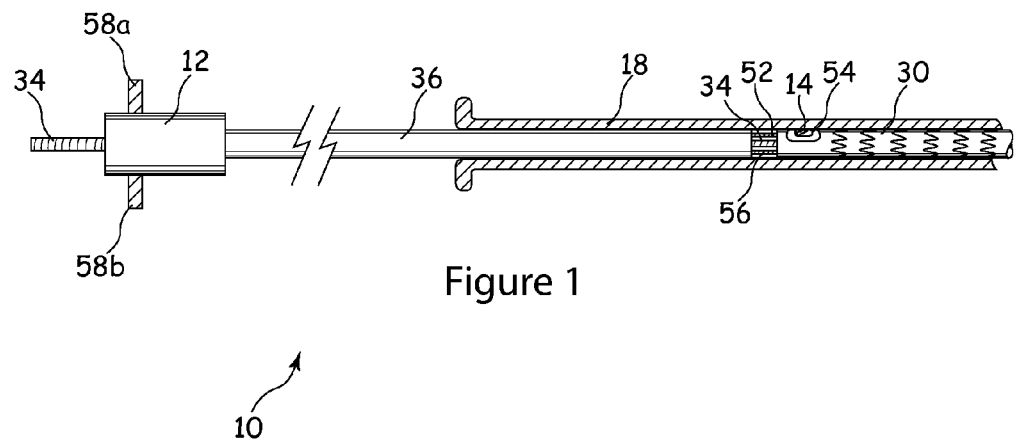
FIG. 1 is a side view of an implant delivery device carrying a compressed implant in accordance with one embodiment of the present invention.

The delivery assembly 10 shown in FIG. 1 includes a handle 12, conventionally made of a plastics material. An inner catheter 36, made of any of the conventional or otherwise suitable catheter materials known in the art, extends from and is attached to the handle 12. An implant 30 is provided at the distal end of the inner catheter 36, and is shown in a compressed state in FIG. 1. The inner catheter 36 has a bore passing longitudinally therethrough for the introduction of a guide wire 34. Surrounding the inner catheter 36 and the implant 30 is an introducer sheath 18. The introducer sheath 18 overlies and acts as a holding sheath for the implant 30.

FIG. 2 shows the release mechanism of a preferred embodiment in more detail. The release mechanism includes a locking element 52 which includes an elongate carrier that extends longitudinally through the bore in the inner catheter 36 from the handle 12 at the proximal end of the delivery assembly 10 to the implant 30 at the distal end of the inner catheter 36. At its distal end the locking element 52 is bent outwardly to form an angled latching pin 14. As the implant 30 is arranged distally of the inner catheter 36, the latching pin 14 of the locking element 52 extends beyond the distal end of the inner catheter 36 to couple the implant 30 to the distal end of the inner catheter 36, in a manner described below.

The implant 30 includes a non-expandable tubular section including an eyelet 54 in a wall thereof. In the example shown in FIGS. 1, 2, 4 to 6 and 8, the tubular section is located at the distal end of the implant 30, but other arrangements are possible. The angled latching pin 14 of the locking element 52 locates into the eyelet 54 in the tubular section of the implant 30, thereby to attach the implant 30 to the distal end of the inner catheter 36.

The delivery assembly 10 is also provided with a blocking member 56, which also extends longitudinally through the bore in the inner catheter 36 from the handle 12 at the proximal end of the delivery assembly 10 to the implant 30. The blocking member 56, in this embodiment, is a longitudinal element which extends into the tubular section of the implant 30 at least as far as the latching pin 14 of the locking element 52.

Figure 3:
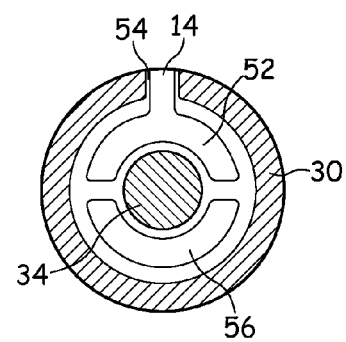
FIG. 3 is a cross-sectional view of the device of FIG. 2 at the line A-A.

A guide wire 34 also extends through the bore of the inner catheter 36 and is arranged such that the locking element 52 and the blocking member 56 lie substantially opposite one another spaced by the guide wire 34 within the bore of the inner catheter 36. As can be seen in FIG. 3, in this embodiment the locking element 52 and the blocking member 56 have a transverse cross section that is substantially crescent shaped. The outer edges of the crescents are located against the wall of the lumen of the inner catheter 36, the inner edges of the crescents together forming a space through which the guide wire 34 extends during delivery of the implant 30. The locking element 52 and the blocking member 56 are sized such that together with the guide wire 34 the bore of the inner catheter 36 is substantially filled with little room for lateral or radial movement of the components. The guide wire may be smaller than 0.1 mm, but more typically may be in the order of 0.5 mm to 1 mm in diameter. The inner diameter of the catheter may be as little as 1 mm, for example.

The locking pin 52 and the blocking member 56 may be made from any suitable material, such as spring steel, stainless steel, Nitinol, polymeric materials etc. They should be flexible enough to allow the delivery assembly 10 to track through a patient's vasculature for delivery of the implant to a site of treatment.

As indicated above, at their proximal ends, the locking element 52 and the blocking member 56 extend to a handle 12 at the proximal end of the delivery assembly 10. More specifically, the locking element 52 is attached to a release knob 58a and the blocking member 56 is attached to a release knob 58b. The release knobs 58 are located within longitudinal slots provided in the handle 12 and are able to slide along the handle 12 in a proximal direction in order to affect withdrawal in a proximal direction of the locking element 52 and the blocking member 56 as described below. An arrangement such as a pin vice arrangement known to those skilled in the art could also be used to effect withdrawal of the locking element 52 and the blocking member 56.

The implant 30 is then introduced by means of the delivery assembly 10 over a guide wire 34 to the site of the patient's vasculature requiring treatment.

The implant 30 is deployed in a vessel of a patient by first introducing a guide wire 34 through an access catheter across the distal segment of a target lesion of the vessel. Once the guide wire 34 is in place, the introducer sheath 18 is fed over the guide wire 34 until the distal end of the introducer sheath 18 is over the target lesion 40. During this process the introducer sheath 18 is flushed with saline solution through a side arm flushing port (not shown).

Once the introducer sheath 18 has been located at the deployment site, the implant 30 held by the delivery assembly 10 is ready to be deployed.

Once the site of the patient's vasculature to be treated has been reached by the distal end of the delivery assembly 10, the introducer sheath 18 is withdrawn in a proximal direction to expose the implant 30. The implant 30 is then allowed to expand. FIG. 4 illustrates the arrangement of the release mechanism after withdrawal of the introducer sheath 18 and expansion of the implant 30. At this stage, if the implant 30 is not quite in the correct location, since it is still attached to the delivery assembly 10 by means of the locking pin 52, the surgeon or clinician is able to manipulate the delivery assembly 10 to enable repositioning of the implant 30.

Figure 5:
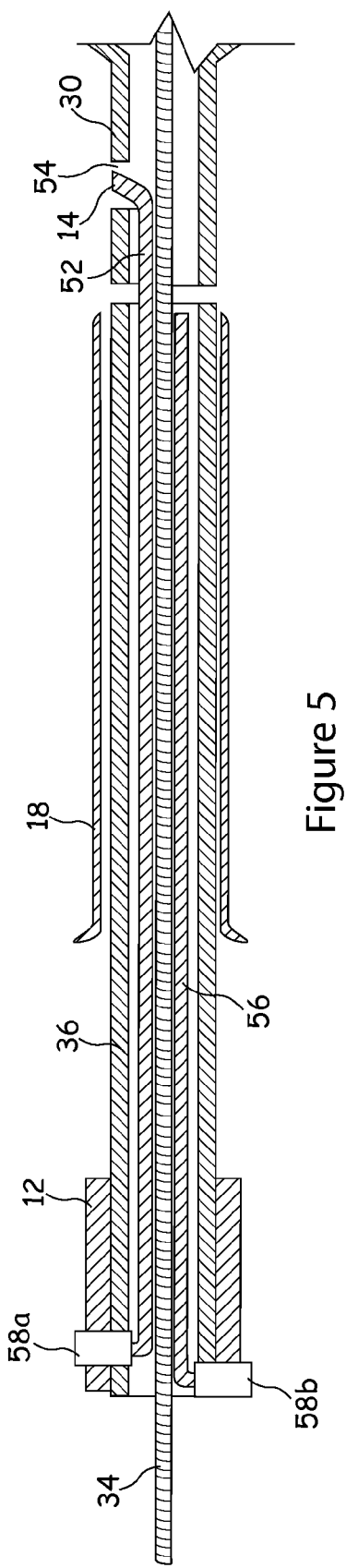
FIGS. 5 and 6 are side cross-sectional views of the implant delivery device of FIGS. 1 to 4 during release of an implant.

Once the implant 30 has been correctly located, the blocking member 56 is withdrawn in a proximal direction by sliding the release knob 58b along the handle 12 in a proximal direction. FIG. 5 shows the blocking member 56 after it has been withdrawn into the inner catheter 36 by proximal movement of the release knob 58b. A space is created within the tubular section of the implant 30, by removal of the blocking member 56, between the guide wire 34 and the wall of the tubular section opposite to the locking pin 52. The locking element 52 remains in place, but because the blocking member 56 has been withdrawn, release and withdrawal of the latching pin 14 are now possible.

The release knob 58a can then be withdrawn in a proximal direction in order to withdraw the locking element 52. Prior to withdrawal of the blocking member 56, the release knob 58a could not be moved proximally because the latching pin 14 of the locking element 52 was hooked into the eyelet 54 of the tubular section of the implant 30. Radially inward movement of the latching pin 14 of the locking element 52 was not possible because there was no space within the tubular section of the implant for this to occur.

Figure 6:
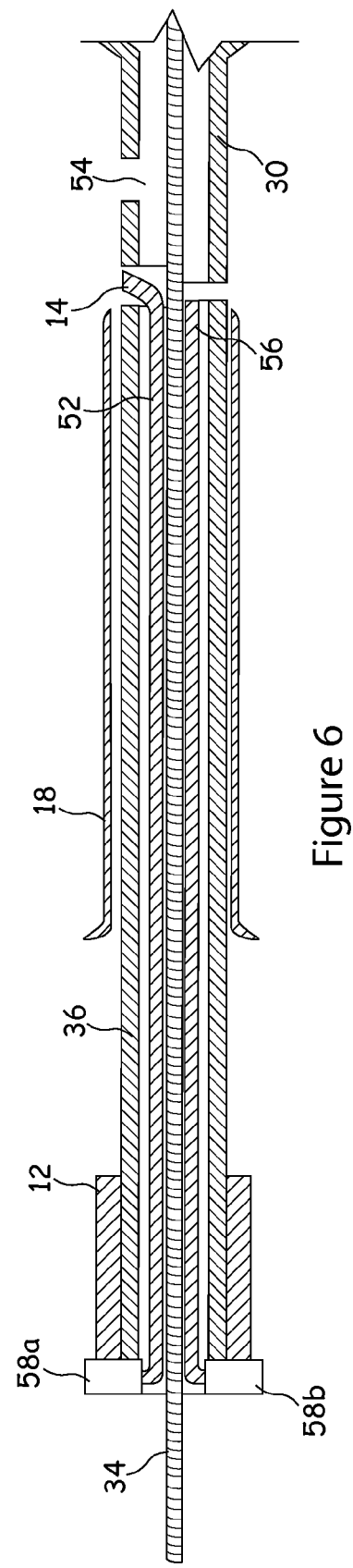

Once the blocking member 56 has been withdrawn, however, the locking element 52 can be manipulated towards the guide wire 34, pushing the guide wire 34 away from the eyelet 54. The latching pin 14 of the locking element 52 is thus able to disengage from the eyelet 54 and be withdrawn towards the inner catheter 36, as illustrated in FIG. 6. The angle of the latching pin 14 is preferably less than 90°. It can thus easily slide past the wall of the eyelet 54. Preferably, the locking pin 52 is biased towards the central longitudinal axis of the lumen of the inner catheter 36. In this way, removal of the blocking member 56 results automatically in the latching pin 14 disengaging from the eyelet 54. At this stage, the implant 30 is free from the delivery assembly 10, which can then be withdrawn leaving the implant 30 in place.

At this stage, however, if the surgeon ascertains that the implant is not quite correctly located, this system allows the implant to be retrieved and repositioned. The release knob 58a can then be moved in a distal direction to push the locking element 52 back into the tubular section of the implant 30. When the release knob 58a is at its most distal position, the latching pin 14 is aligned with the eyelet 54. Some rotation of the delivery assembly 10 may be required to enable the latching pin 14 to engage with the eyelet 54. The surgeon then reengages the blocking member 56 by distally moving the release knob 58b to engage the latching pin 14 with the eyelet 54.

This process can be repeated as necessary until the implant 30 is correctly located at which time the delivery assembly 10 can be withdrawn leaving the implant 30 in place.

It can be seen from the above that the described release mechanism allows an implant 30 to be detached from a delivery assembly 10 in a controlled manner. Furthermore, the release mechanism is compatible with over-the-wire delivery, which offers important advantages over the prior art. The blocking member 56 prevents premature disengagement of the locking element 52, and the arrangement enables the surgeon to make fine adjustments to the position of the implant 30 in situ.

In addition, where an implant 30 is temporary, the retrieval function of the release mechanism can be used to retrieve and remove an implant 30 from a patient. In order to retrieve a previously deployed implant 30, the implant deployment device 10 is once again introduced into a patient over a guide wire 34 to the location of the previously implanted implant 30. The locking element 52 is moved in a distal direction so that the latching pin 14 can re-engage with the eyelet 54. Re-engagement is completed by distal movement of the blocking member 56, which thus pushes the latching pin 14 back into the eyelet 54. Withdrawal of the inner catheter 36 then allows the implant to be withdrawn back into the sheath 18 for removal.

The locking element 52 and blocking member 56 take up very little space and can be used with an inner catheter 36 having an inner diameter of only 1 mm.

Although the embodiments disclosed above have been described in connection with a substantially conical occlusion device it may be used with any other type of occlusion device, for example, an hourglass-shaped occlusion device. In such a case, the tubular section could be provided at a substantially central part of the implant. Other arrangements may be envisaged.

Figure 7:
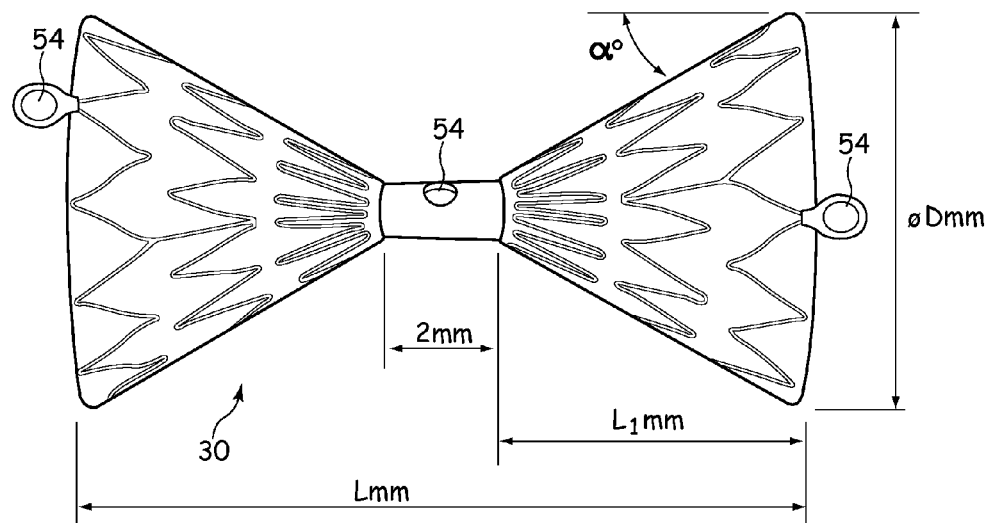
FIGS. 7 and 8 are side views of exemplary retrievable devices.
Figure 8:
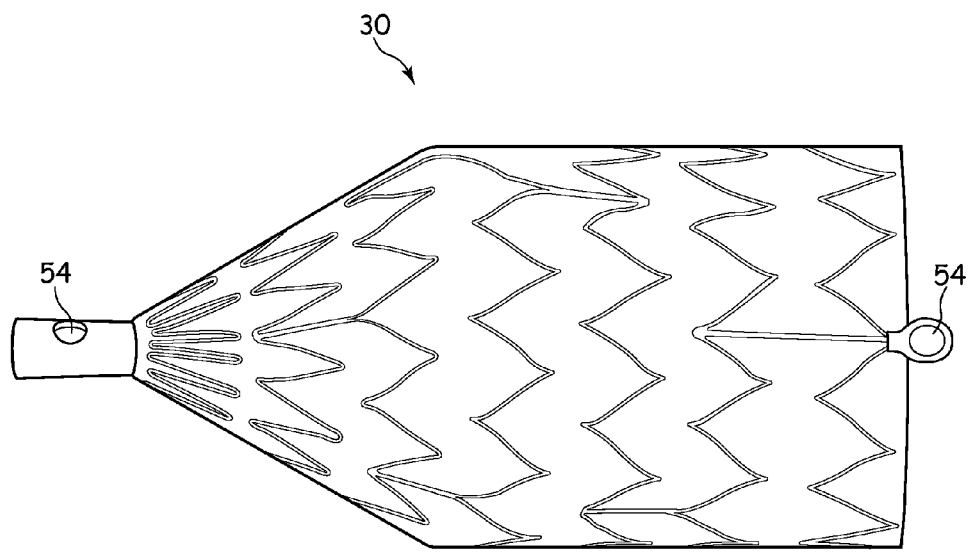

FIGS. 7 and 8 illustrate examples of retrievable occlusion devices 30. The eyelet 54 may be a 0.5 mm aperture. Several eyelets 54 may be provided in the tubular section of the implant 30. For example, two eyelets 54 arranged at approximately 180° from one another, or three eyelets arranged at approximately 120° from one another. Providing a plurality of eyelets assists in re-engaging the locking pin 14 during retrieval of an implant 30.

FIG. 7 also shows typical dimensions for a device 30, further details of which are given in Table 1 below:

TABLE 1

|  | Lmm | L1mm | ϕDmm |
|---|---|---|---|
| α = 45° | 11.8 | 4.9 | 9.8 |
| α = 60° | 9.0 | 3.5 | 12.0 |
| α = 30° | 14.0 | 6.0 | 7.0 |

The implant 30 is typically formed from Nitinol tubing and typically has an outside diameter of 1 mm and a wall thickness of 0.16 mm. The Z-pattern provides a suitable framework for a covering material that provides occlusion. The covering material can be modified to have a low friction outer surface to reduce resistance during insertion. Preferably, three eyelets 54 are provided at each end of the device 30.

Figure 9:
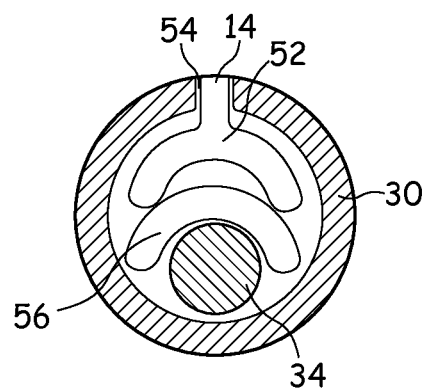
FIG. 9 is a cross-sectional view of an implant delivery device in accordance with another embodiment of the present invention.

Other modifications are, of course, possible. FIG. 9 illustrates an embodiment in which the locking element 52 and the blocking member 56 are both provided on the same side of a guide wire 34. The precise arrangement is unimportant. However, it can be seen that disengagement of the latching pin 14 from the eyelet 54 of the implant 30 is possible only after withdrawal of the blocking member 56. Other arrangements may also be envisaged.

Further, this release mechanism can be used with any implant which can be carried by such a delivery device. It can be used, for example, to hold any other type of frame, a frame with a graft, a filter, or any other implant or prosthesis deliverable by such a delivery device.

The described handle 12 is merely exemplary. Other handles suitable for effecting withdrawal of a blocking member 56 and a locking element 52 are, of course, possible.

The skilled person will appreciate that many other modifications are possible.

The disclosures in U.S. 61/072,903, from which this application claims priority, and in the accompanying abstract are incorporated herein by reference.

While the present invention has been described in terms of preferred embodiments, it will be understood, of course, that the invention is not limited thereto since modifications may be made to those skilled in the art, particularly in light of the foregoing teachings.

The invention claimed is:

1. An implant release mechanism for use over a guide wire (34), including:
   a deployment device (10) with a catheter (36); a releasable coupling member (14, 52) for maintaining attachment of an implant (30) to be deployed to the deployment device (10), the releasable coupling member having an elongate carrier and a distal end forming a latching pin bent radially outward; and
   a blocking member (56) for blocking release of the releasable coupling member by blocking a radially inward movement of the elongate carrier;
   wherein removal of the blocking member allows release of the coupling member, and thus detachment of an implant,
   wherein the releasable coupling member (14, 52) and an elongate body of the blocking member (56) extend longitudinally through a bore of the catheter (36) of the deployment device (10) beside each other and parallel to a longitudinal channel for a guide wire (34), wherein an outer surface of the elongate carrier and an outer surface of the elongate body of the blocking member are in contact with each other.

2. The mechanism of claim 1 wherein the releasable coupling member (52) is operable to reattach a released implant to the deployment device (10).

3. The mechanism of claim 1 wherein the releasable coupling member (14, 52) is arranged to attach an implant (30) distally of the catheter (36) of the deployment device (10).

4. The mechanism of claim 1 wherein the releasable coupling member (14, 52) and the blocking member (56) together have a size configured to partially fill a lumen of an implant-coupling portion of the implant containing a guide wire (34).

5. The mechanism of claim 1 wherein the releasable coupling member (14, 52) extends longitudinally through a bore of the catheter (36) of the deployment device (10) from a handle (12) at a proximal end of the deployment device to a location of the implant (30) at the distal end of the catheter (36), and wherein the distal end (14) of the releasable coupling member (52) is configured to engage with the implant.

6. The mechanism of claim 1 wherein the releasable coupling member (14, 52) latching in (14) is able to engage with the implant (30).

7. The mechanism of claim 6 wherein the blocking member (56) prevents disengagement of the latching pin from the implant (30).

8. The mechanism of claim 1, wherein the deployment device (10) comprises a release mechanism.

9. The mechanism of claim 8 further comprising an implant (30) for delivery by the device (10), the implant including an engagement portion (54) for coupling to the releasable coupling member (14, 52).

10. The mechanism of claim 9 wherein the engagement portion includes an aperture (54).

11. The mechanism of claim 10 wherein the engagement portion (54) includes a substantially tubular member having an aperture (54) in a wall thereof.

12. The mechanism of claim 9 wherein the engagement portion (54) includes a substantially non-expandable tubular member.

13. The mechanism of claim 9 wherein the implant is one of an occlusion device, a frame, a frame with a graft, and a filter.

14. The mechanism of claim 13 wherein the implant is an occlusion device that provides substantially immediate vascular occlusion.

15. The mechanism of claim 9 wherein the implant (30) is attached to the device by the releasable coupling member (14, 52).

16. The mechanism of claim 1 wherein at least one of the releasable coupling member (14, 52) and the blocking member (56) has a transverse cross section that is crescent-shaped such that it extends along a portion of an inner wall of the catheter (36) of the deployment device (10).

17. An implant release mechanism for use over a guide wire (34), including:
   a deployment device (10) with a catheter (36);
   a releasable coupling member (14, 52) for maintaining attachment of an implant (30) to be deployed to the deployment device (10); and
   a blocking member (56) for blocking release of the coupling member;
   wherein removal of the blocking member allows release of the coupling member, and thus detachment of an implant,
   wherein the releasable coupling member (14, 52) and the blocking member (56) extend longitudinally through a bore of the catheter (36) of the deployment device (10) parallel to a longitudinal channel for a guide wire (34), wherein the releasable coupling member and the blocking member are arranged approximately 180° from one another with respect to a longitudinal central axis of the catheter, and wherein the releasable coupling member and the blocking member together define the longitudinal channel for the guide wire (34).

* * * * *